(12) United States Patent
Kim (10) Patent No.: US 7,037,279 B2
(45) Date of Patent: May 2, 2006

(54) LIE-DOWN MASSAGER

(76) Inventor: Hakjin Kim, 610 Ridgeview Ct., Diamond Bar, CA (US) 91765

( * ) Notice: Subject to any disclaimer, the term of this patent is extended or adjusted under 35 U.S.C. 154(b) by 431 days.

(21) Appl. No.: 10/445,517

(22) Filed: May 27, 2003

(65) Prior Publication Data

US 2004/0243034 A1   Dec. 2, 2004

(51) Int. Cl.
*A61H 7/00* (2006.01)
*A61H 15/00* (2006.01)

(52) U.S. Cl. ............... 601/18; 601/19; 601/98; 601/99; 601/103; 601/116

(58) Field of Classification Search ............ 601/15, 601/17, 18, 19, 86, 87, 90–96, 97–99, 100–103, 601/115, 116, 122, 126; 606/240–242
See application file for complete search history.

(56) References Cited

U.S. PATENT DOCUMENTS

| | | | |
|---|---|---|---|
| 2,193,882 A | 3/1940 | Petersen |
| 2,310,106 A | 2/1943 | Miller |
| 2,359,933 A | 10/1944 | Niblack |
| 2,781,040 A | 2/1957 | Hill |
| 2,874,689 A | 2/1959 | Gavelek |
| 2,909,173 A | 10/1959 | Anderson |
| 3,687,133 A | 8/1972 | Grubelic |
| 3,877,422 A | 4/1975 | Heuser et al. |
| 4,190,043 A | 2/1980 | Thompson |
| 4,422,449 A | 12/1983 | Hamabe |
| 4,458,675 A | 7/1984 | Nakao et al. |
| 4,586,493 A | 5/1986 | Goodman |
| 4,656,998 A | 4/1987 | Masuda et al. |
| 4,899,403 A | 2/1990 | Yamasaki |
| 4,947,833 A | 8/1990 | Yamasaki |
| 5,038,757 A | 8/1991 | Yamasaki |
| 5,088,475 A | 2/1992 | Steffensmeier |
| 5,165,390 A | 11/1992 | Fleetwood |
| 5,179,940 A | 1/1993 | Barreiro |
| 5,755,677 A | 5/1998 | Masuda et al. |
| 5,807,288 A | 9/1998 | Wu |
| 6,071,252 A | 6/2000 | Marcantoni |
| 6,190,338 B1 | 2/2001 | Arndt |
| 6,224,563 B1 | 5/2001 | Nonoue et al. |
| 6,243,609 B1 | 6/2001 | Lee |
| 6,409,689 B1 | 6/2002 | Chen |

(Continued)

*Primary Examiner*—Quang D. Thanh
(74) *Attorney, Agent, or Firm*—Park Law Firm; John K. Park (57) ABSTRACT

A lie-down massager includes a base frame having an elongated top panel, through which an elongated top opening is formed centrally and lengthwise, a rider provided below the elongated top panel of the base frame, a guide member movably engaged between the base frame and the rider so as to enable the rider to make a horizontally reciprocal movement relative to the base frame, massage bumps that move vertically and/or horizontally along the elongated top opening of the elongated top panel of the base frame, and a lifter that holds the massage bumps and adjusts the height of the massage bumps. The lifter includes two vertical screws that rotates together by a chain and two nuts engaging with the screws so that rotating the screws lift or lower the nuts thereby adjusting the height of the massage bumps. A motor rotates the screws via a worm gear.

25 Claims, 10 Drawing Sheets

U.S. PATENT DOCUMENTS

| | | |
|---|---|---|
| 6,454,732 B1 | 9/2002 | Lee |
| 6,542,779 B1 | 4/2003 | Lee |
| 6,555,798 B1 | 4/2003 | Lee |
| 6,629,939 B1 | 10/2003 | Jikiba et al. |
| 6,643,551 B1 | 11/2003 | Park |
| 2002/0138023 A1 | 9/2002 | Kume et al. |
| 2002/0193713 A1 | 12/2002 | Lee |
| 2003/0018284 A1 | 1/2003 | Lim |

LIE-DOWN MASSAGER

BACKGROUND OF THE INVENTION

The invention relates generally to a massaging device. More particularly, the present invention relates to an improved lie-down massager capable of efficiently treating bodily malfunctions such as back pain and gastrointestinal weakness by applying a therapeutic massaging treatment along the back and neck of a patient lying down on the massager whose massaging bumps move horizontally and vertically along the patient's spinal cord and neck while the vertical movement of the massaging bumps are actuated by a vertical screw lifting mechanism.

Conventional bed or mat type massaging devices employ a spring mechanism for vertically moving massaging bumps. As disclosed U.S. Pat. No. 6,454,732, a spring mechanism allows the massaging bumps to gently move up and down. However, when it comes to therapeutic effects, the spring mechanism proves too soft to push up the massaging bumps when stronger pressure is required, because tension of springs applies equally to patients lying on the massaging device regardless of patient's requirements.

A demand is to adopt a reliable mechanism demonstrating a steady and robust therapeutic effects while stabilizing the vertical movement of the massaging bumps.

SUMMARY OF THE INVENTION

The present invention is contrived to overcome the conventional disadvantages. Accordingly, an object of the invention is to provide a lie-down massager that improves therapeutic effects by adopting a screw lifting mechanism for a vertical movement of massaging bumps.

Another object is to stabilize the vertical movement of the massaging bumps, thereby enabling patients to receive a steady and robust massaging of the massaging bumps applied to and along their backs and necks. A further object is to improve product reliability and customer satisfaction by mechanically stabilizing the vertical movement of the massaging bumps.

To achieve these and other objects, the lie-down massager according to the present invention includes a base frame having an elongated top panel, through which an elongated top opening is formed centrally and lengthwise, a rider provided below the elongated top panel of the base frame, a guide member movably engaged between the base frame and the rider so as to enable the rider to make a horizontally reciprocal movement relative to the base frame, a lifter having a top plate and a bottom plate, a first nut, a first screw, and a motor, a plurality of massage bumps attached to the top plate of the lifter and moving vertically and/or horizontally along the elongated top opening of the elongated top panel of the base frame, and a pad covering the massage bumps and the elongated top opening of the base frame.

In the lifter, the top plate has a top upper surface portion and a top lower surface portion. The bottom plate has a bottom upper surface portion and a bottom lower surface portion. The first screw is vertically and rotationally attached to the bottom upper surface portion, and the first nut is fixed to the top lower surface portion. The first screw engages with the first nut so that rotation of the first screw lifts the first nut or lowers the first nut. The motor rotates the first screw in either clockwise or counterclockwise direction.

The lifter may further include a second screw vertically and rotationally attached to the bottom upper surface portion, and a second nut fixed to the top lower surface portion. The second screw engages with the second nut so that rotation of the second screw lifts the second nut or lowers the second nut. The first screw and the second screw are spaced from each other by a predetermined distance. The first screw and the second screw are connected by a power transmission device so that they rotate together. The first screw and the second screw may be integrated with the top plate of the lifter.

The power transmission device includes a first sprocket that is fixed to the first screw, a second sprocket that is fixed to the second screw, and a chain that is wound around the first sprocket wheel and the second sprocket wheel. A motor rotates the first screw via a worm wheel fixed to the first screw, and a worm gear fixed to the motor.

The massage bumps are partitioned to first and second pairs, and the first pair bumps are aligned parallel to the second pair bumps. The massage bump includes a heater that is a heating lamp generating heat and infrared rays.

First and second bump holders are provided for propping and maintaining the first and second pair bumps above the top portion of the lifter. The first and second bump holders are tapered toward each lower end thereof. Also a first engagement member to rockingly engage the lower ends of the bump holders to the top portion of the lifter, and a second engagement member to rollingly engage the massage bumps thereto are provided. The massage bumps are roller balls that are formed of jade.

Alternatively, the massage bumps are provided as round projections that are fixed to the top upper surface portion of the lifter.

The guide member includes one or more roller gear engaged to and powered by a roller gear motor, and one or more side rack gears parallel to each other and provided lengthwise in the base frame. The roller gear motor is fixed to the rider, and the roller gears are rollably connected to the rider and rotatably mounted on the side rack gears.

Alternatively, the guide member includes rider guide rollers provided on each side of the rider, and a pair of pulleys linked by a rope and respectively mounted in a front end portion and a rear end portion of the base frame. The rider guide rollers are rollably engaged to the base frame to guide a horizontally reciprocal movement of the rider. A predetermined portion of the rope is fixedly attached to the rider so that the pulley rotation enables the rider to generate a horizontally reciprocal movement of the rider. The pulleys are relatively twisted by 90 degrees against each other.

The lie-down massager further includes a pair of roller coasters parallel to each other, and coaster guide rollers formed outwardly extending from each side of the lifter. The roller coasters are attached to the base frame, and each of the roller coasters has a substantially waved top surface. The coaster guide rollers enable the coasting member to make a roller coasting movement on and along the waved top surfaces of the roller coasters. Each of the waved top surfaces of the roller coasters substantially forms a curvature of a human spinal cord.

The bottom plate of the lifter further includes a plurality of elongated guides extending downward from the bottom portion, and the rider further comprises a plurality of guide bushes upwardly formed on the rider to releasably receive the elongated guides so as to stabilize the roller coasting movement of the lifter along the roller coasters. The elongated guides are shaped in pins.

Advantages of the present inventions include that: (1) the screw lifting mechanism minimizes parts required for the vertical movement of the massaging, while improving stability in the vertical reciprocation of the lifter carrying the massaging bumps; (2) the screw lifting mechanism provides smooth and quite operation of the lifter; and (3) the coasting member working with the roller coasters to realize an additional lifting by utilizing the horizontally reciprocal movement of the rider enables the massaging bumps to continue a smooth, steady and robust massaging on the patient, thereby substantially improving massaging effect and subsequently maximizing customer satisfaction.

Although the present invention is briefly summarized, the full understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENTS

Figure 1:
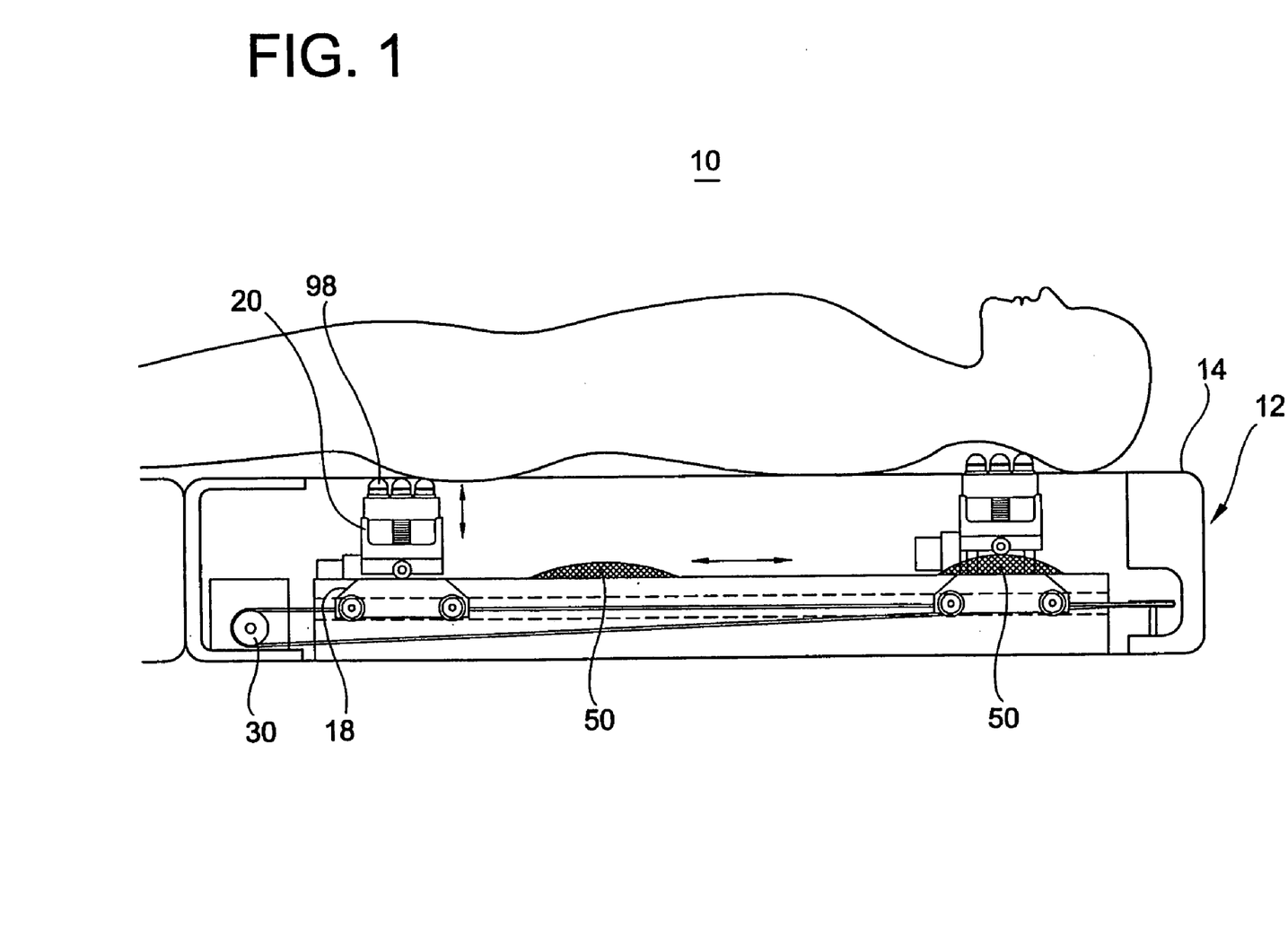
FIG. 1 is a view showing a lie-down massager with a patient lying thereon according to the present invention.
Figure 2:
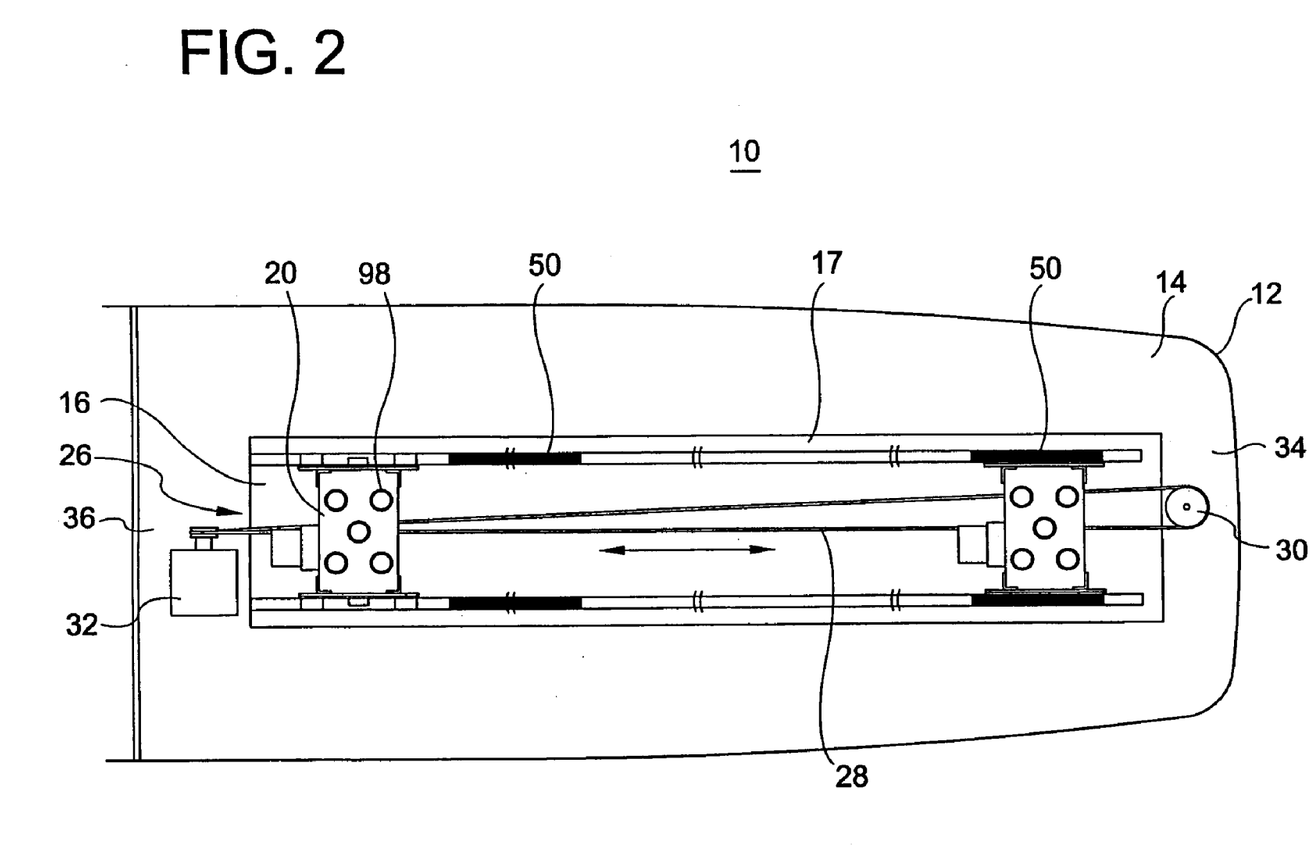
FIG. 2 is a plan view showing the lie-down massager without the patient in FIG. 1.

FIG. 1 shows a brief massaging mechanism of a lie-down massager 10 according to the present invention with a patient lying thereon for a bodily massage, and FIG. 2 shows a plan view of the massager 10 excluding the patient. As shown therein, the lie-down massager 10 includes a base frame 12 in a bed type or a mat type. The base frame 12 includes an elongated top panel 14, and an elongated opening 16 is formed centrally and lengthwise through the elongated top panel 14. The massager 10 includes a rider 18 and a lifter 20. The rider 18 is provided below the elongated top panel 14 of the base frame 12.

In order to implement the horizontal reciprocation of the rider 18, there is provided a guide member 26 movably engaged between the base frame 12 and the rider 18 so as to enable the rider 18 to make a horizontally reciprocal movement relative to the base frame 12. Here, it is recommended that the guide member 26 be either a rope-pulley application or a rack gear application.

Figure 3:
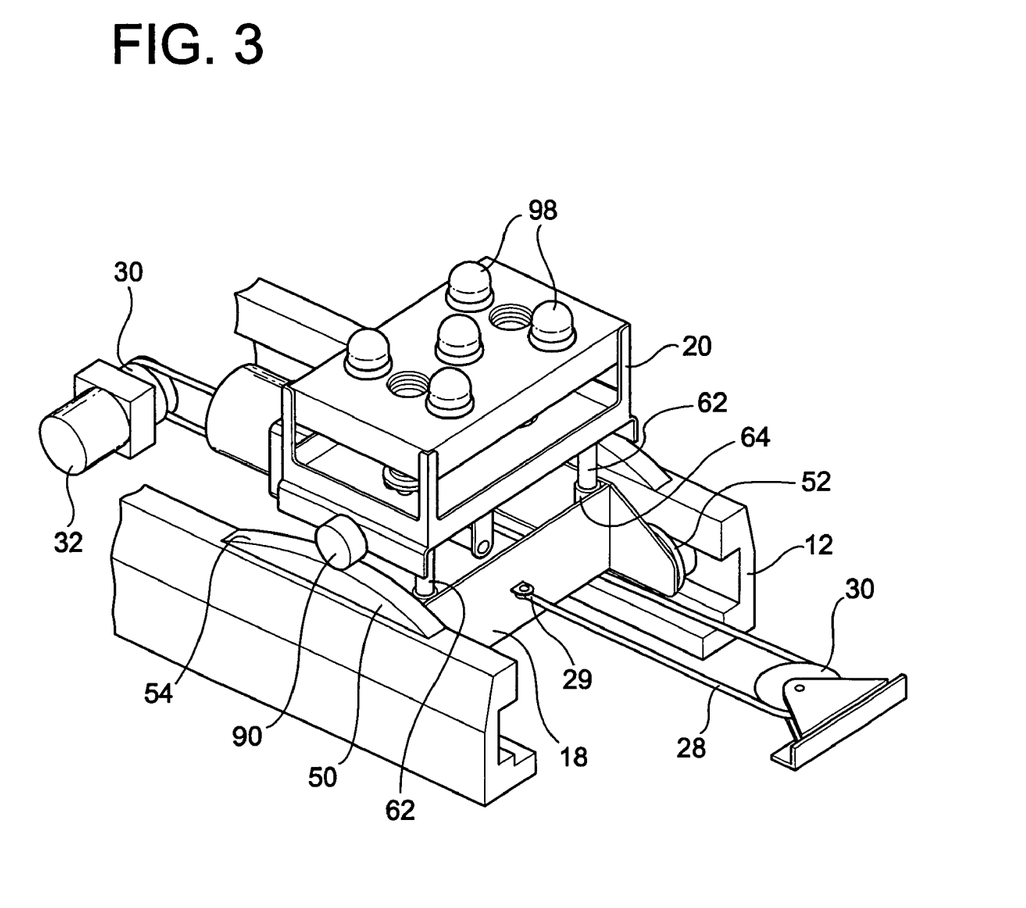
FIG. 3 is a partial perspective view showing an overall mechanism of the lie-down massager according to a first embodiment of the present invention.

As shown in FIG. 2 together with FIG. 3, the guide member 26 according to the rope-pulley application includes a rope 28, a pair of pulleys 30 and a pulley motor 32 that controls one of the pulleys 30. The pulleys 30 are linked by the rope 28 and respectively mounted in a front end portion 34 and a rear end portion 36 of the base frame 12. In a preferred version, the pulley motor 32 is provided adjacent to the pulley 30 provided in the rear end portion 36 of the base frame 12. In this construction, a predetermined portion 29 of the rope 28 is fixedly attached to the rider 18 so that the pulley rotation enables the rider 18 to generate a horizontally reciprocal movement of the rider 18. Preferably, the pulleys 30 are relatively twisted by 90 degrees against each other to facilitate the horizontal reciprocation of the rider 18 while improving controllability of the rider reciprocation.

Figure 4:
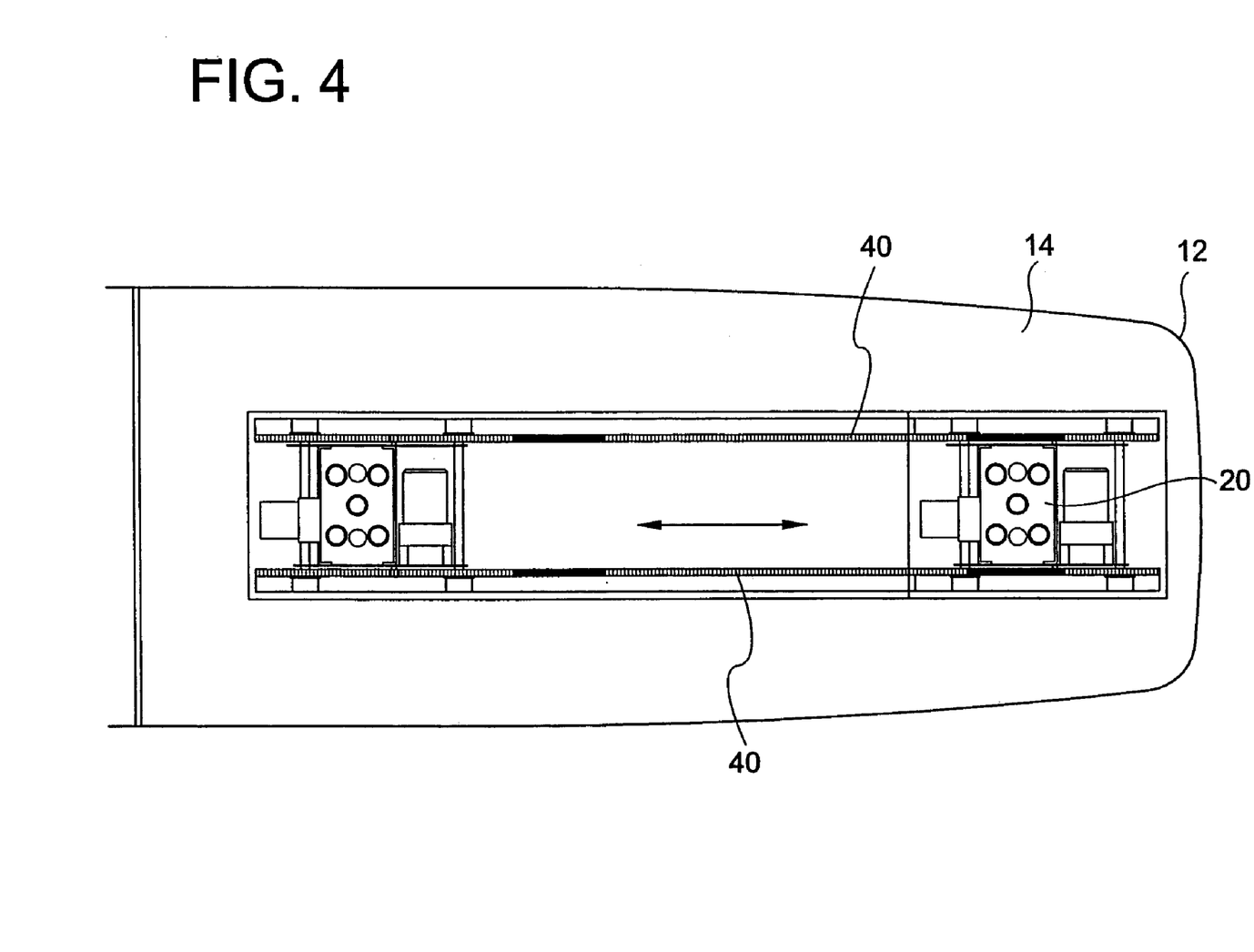
FIG. 4 is a partial plan view showing a second embodiment of the present invention.
Figure 5:
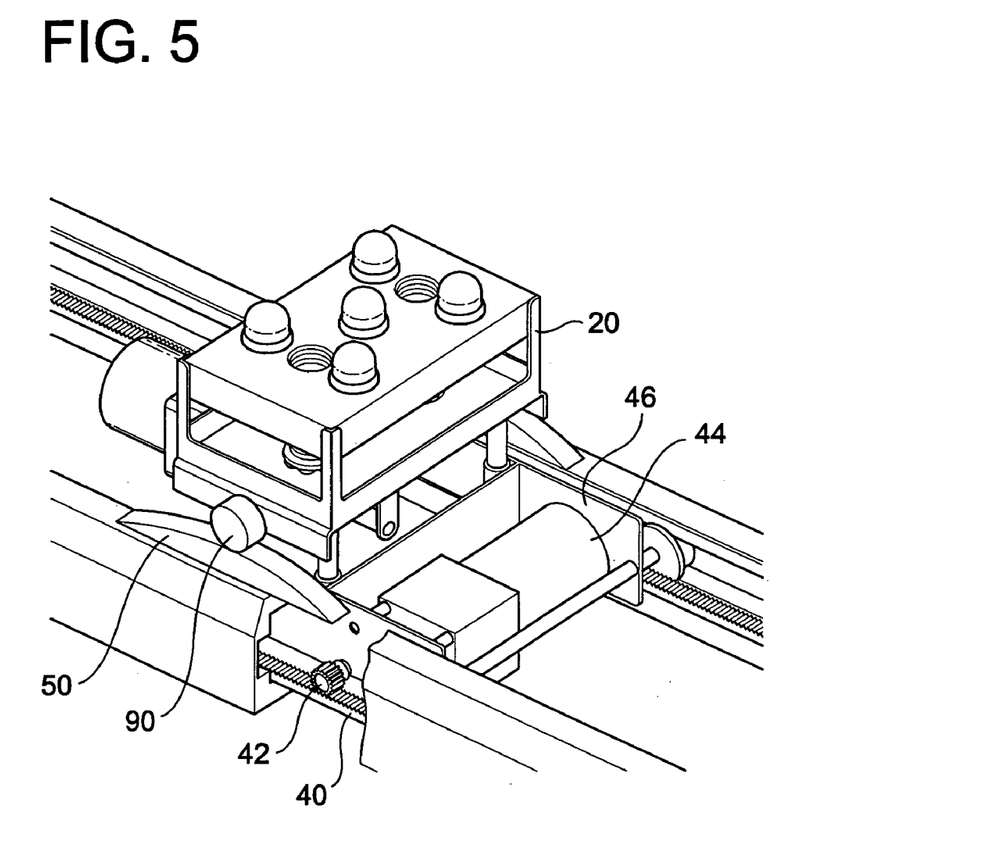
FIG. 5 is a partial perspective view showing the mechanism according to the second embodiment of the present invention.
Figure 6:
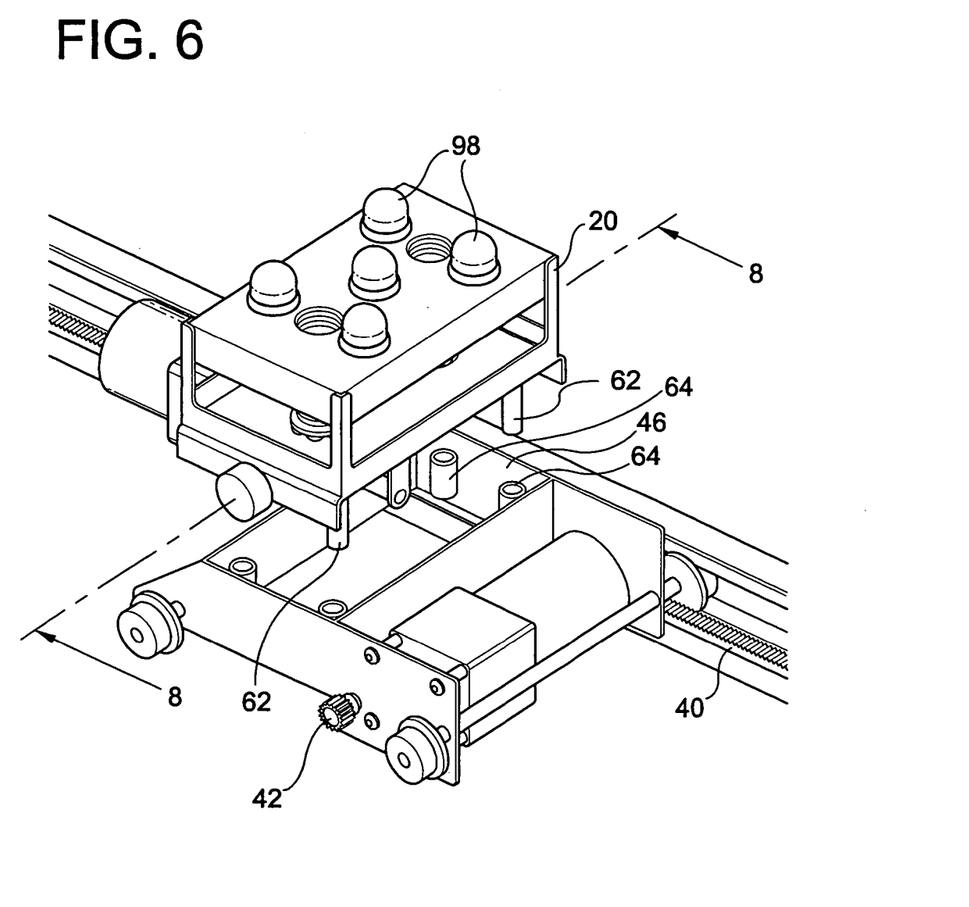
FIG. 6 is a partial exploded perspective view showing the rider and the lifter.
Figure 7:
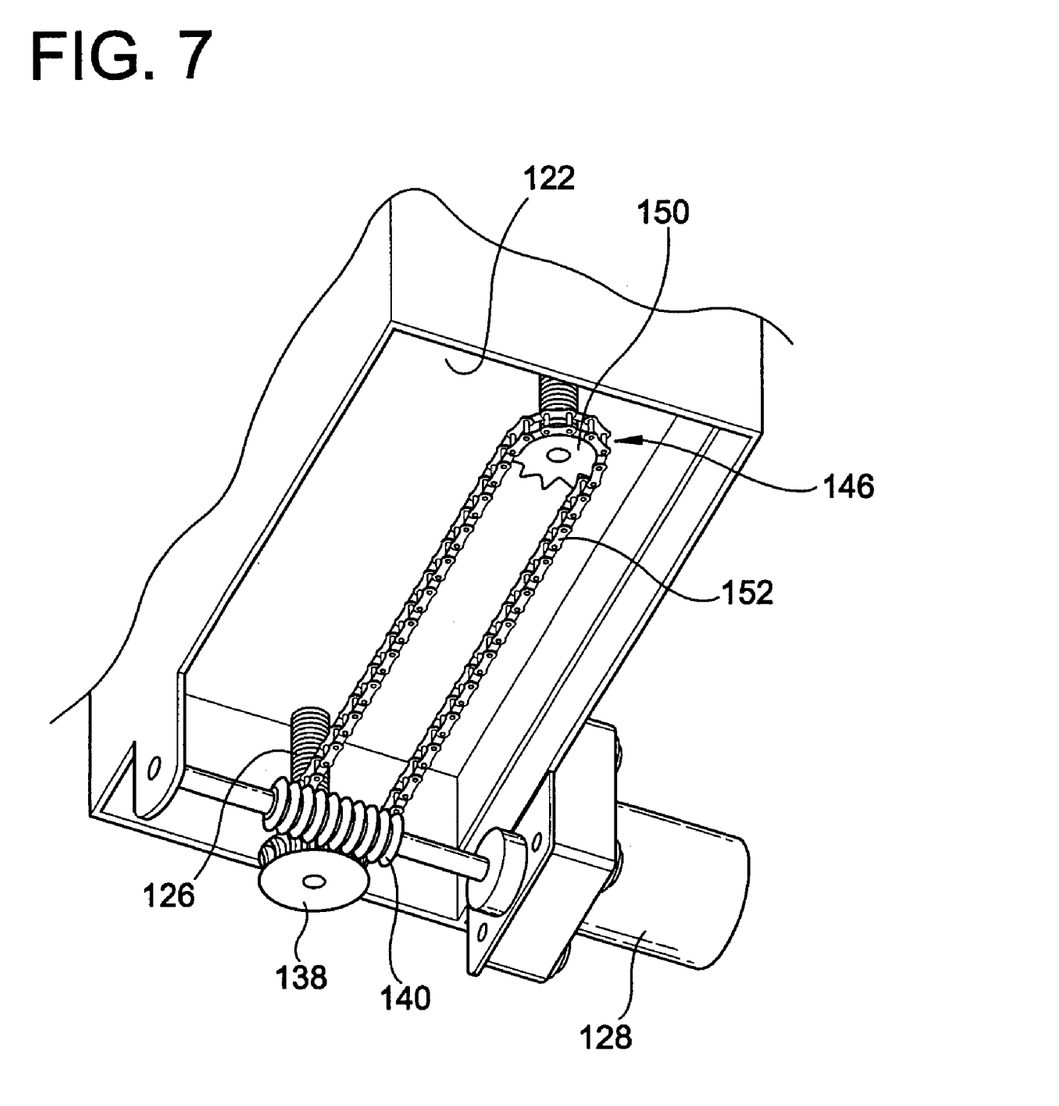
FIG. 7 is a perspective view of the lifter viewed under the lifter.

Meanwhile, FIGS. 4, 5 and 6 respectively illustrate the rack gear application for the horizontal reciprocation of the rider 18. As shown therein, the guide member 26 employing the rack gear application includes a pair of side rack gears 40 parallel to each other and lengthwisely provided in the base frame 12, a roller gear 42 perpendicular to the side rack gears 40, and a roller gear motor 44 fixed to the rider to power the roller gear 42. The roller gear 42 is rollably connected to a rider 46 and rotatably mounted on the side rack gears 40.

To accelerate massaging effect, the massager 10 includes one or more pairs of roller coasters 50 parallel to each other. The roller coasters 50 are attached to the base frame 12 and above the rider guide rollers 52 formed on each side of the rider 18(refer to FIG. 3). The rider guide rollers 52 are rollably engaged to the base frame 12 to guide a horizontally reciprocal movement of the rider 18. That is, the roller coasters 50 are formed on each side of the base frame 12. Here, the roller coasters 50 each have a substantially waved top surface 54. It is preferred that the waved top surfaces 54 of the roller coasters 50 each substantially form a curvature of a human spinal cord.

In order to utilize the roller coasters 50, there are provided two coaster guide rollers 90 formed outwardly extending from each side of the lifter 20. The coaster guide rollers 90 enable the lifter 20 to make a roller coasting movement on and along the waved top surfaces 54 of the roller coasters 50.

Figure 8:
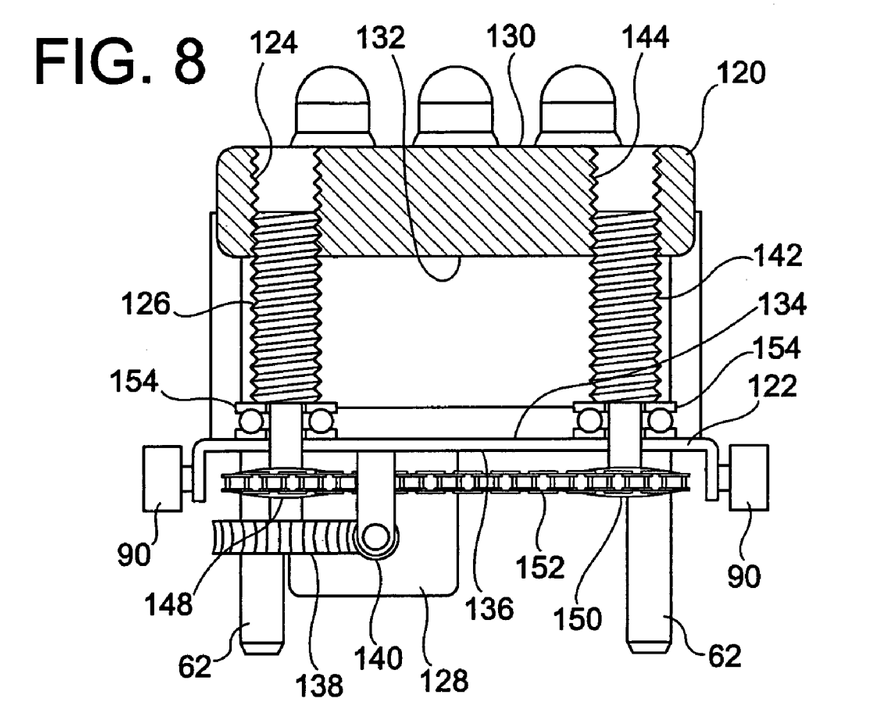
FIG. 8 is a cross-sectional view of the lifter taken along the line 8–8 in FIG. 6.
Figure 9:
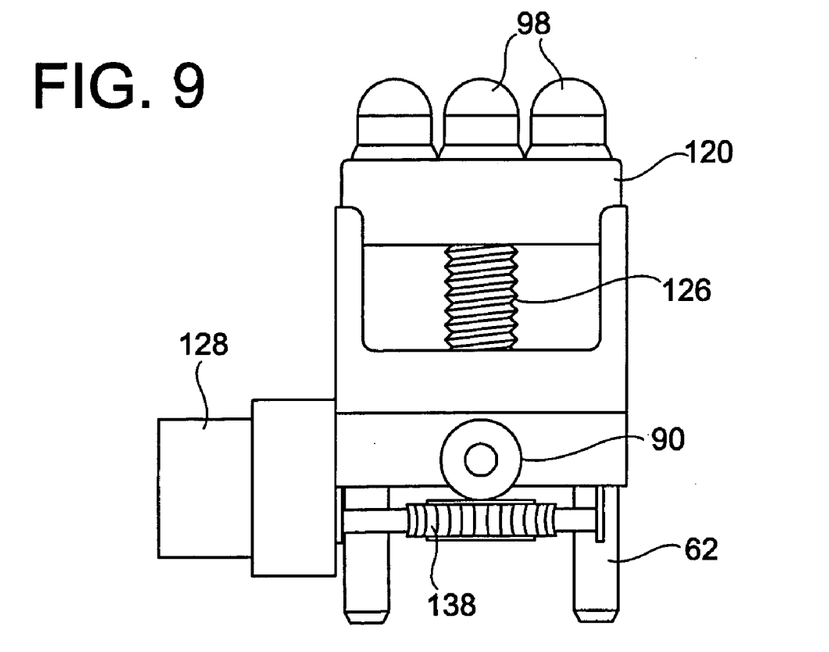
FIG. 9 is a side elevation view of the lifter.

As shown in FIGS. 7–11, the lifter 20 has a top plate 120, a bottom plate 122, a first nut 124, a first screw 126, and a motor 128. The top plate 120 has a top upper surface portion 130 and a top lower surface portion 132. The bottom plate 122 has a bottom upper surface portion 134 and a bottom lower surface portion 136. The first screw 126 is vertically and rotationally attached to the bottom upper surface portion 134 with a bearing 154. The first nut 124 may be fixed to the top lower surface portion 132, or integrated with the top plate 120 as shown in FIG. 8. The first screw 126 engages with the first nut 124 so that rotation of the first screw 126 lifts the first nut 124 or lowers the first nut 124. The motor 128 rotates the first screw 124 in either clockwise or counterclockwise direction via a worm wheel 138 fixed to the first screw 126, and a worm gear 140 fixed to the motor 128.

The lifter further comprises a second screw 142 vertically and rotationally attached to the bottom upper surface portion 134 with a bearing 154, and a second nut 144 that may be fixed to the top lower surface portion 132. The second nut 144 is integrated with the top plate 120. The second screw 142 engages with the second nut 144 so that rotation of the second screw 142 lifts the second nut 144 or lowers the second nut 144. The first screw 126 and the second screw 142 are spaced from each other by a predetermined distance. The first screw 126 and the second screw 142 are connected by a power transmission device 146 so that they rotate together. The male threads of the first screw 126 and the second screw 142 are the same, and the first nut 124 and the second nut 144 have corresponding female threads.

The thread engagement between the screws 126, 142 and the nuts 124, 144 provide smooth, fine and silent operation of lifting or lowering the top plate 120 and thus, the massage bumps 98.

Elongated guides 62 downwardly extend from the bottom lower surface portion 136 of the lifter 20, and guide bushes 64 are upwardly formed on the rider 18 to releasably receive the elongated guides 62 so as to stabilize the roller coasting movement of the lifter 20 along the roller coasters 50. Preferably, the elongated guides 62 are shaped in pins.

The power transmission device 146 includes a first sprocket 148 that is fixed to the first screw 126, a second sprocket 150 that is fixed to the second screw 142, an a chain 152 that is wound around the first sprocket wheel 148 and the second sprocket wheel 150.

Since the first screw 126 and the second screw 142 are rotated simultaneously in the same direction by the power transmission device 146, balanced and stabilized lifting and lowering operations of the top plate 120 is provided.

Two side walls 156 extend downward from two opposing ends of the bottom plate 122, and the coaster guide rollers 90 are rotatably attached to the side walls 156.

Four corner guides 158 extend upward from the corners of the rectangular bottom plate 122. The corner guides 158 guide and protect the four corners of the rectangular top plate 120 when it is moved up and down.

In order to finally apply the screw lifting mechanism to a patient lying on the massager 10, there are provided five massage bumps 98 attached to the top upper surface portion 130 of the lifter 20 and moving vertically and/or horizontally along the elongated top opening 16 of the elongated top panel 14 of the base frame 12 (refer to FIG. 3). Optionally, a pad 17 may be provided to cover the massage bumps 98 and the elongated top opening 16 of the base frame 12.

The massage bumps 98 are round projections that are fixed to the top upper surface portion 130 of the lifter 20.

Figure 10:
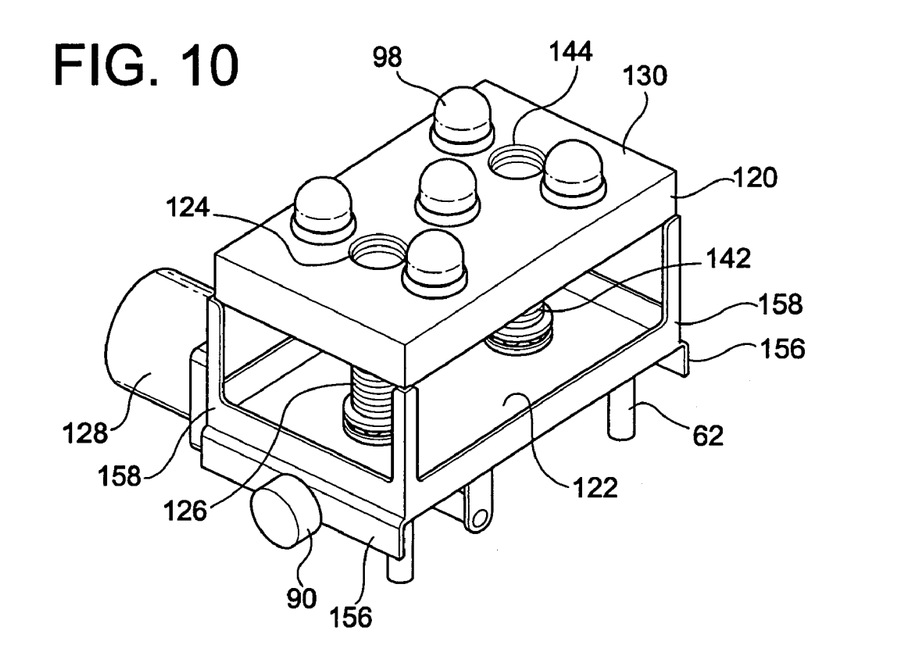
FIG. 10 is a perspective view showing that the lifter is in its highest position.
Figure 11:
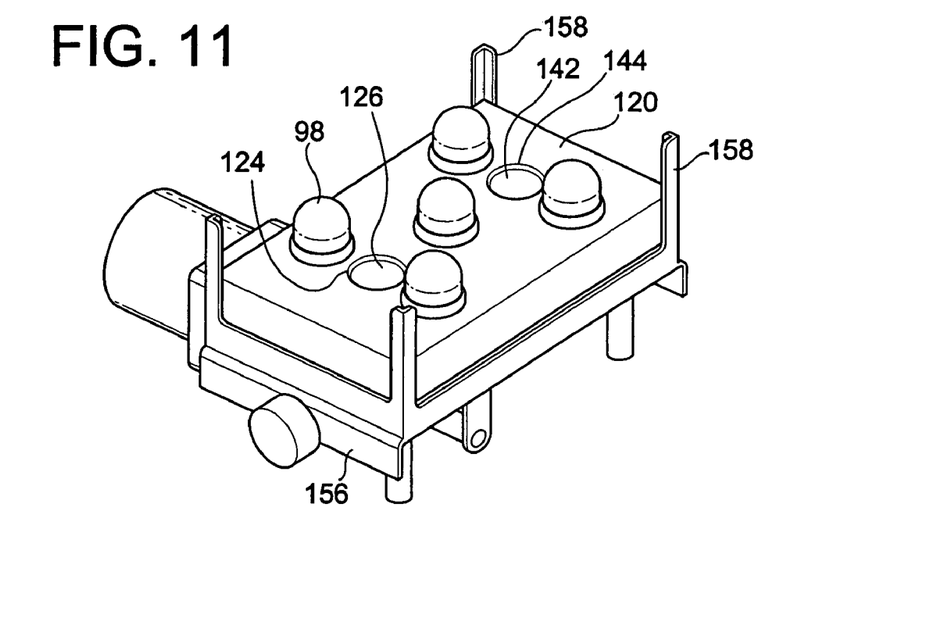
FIG. 11 is a perspective view showing that the lifter is in its lowest position.

FIG. 10 shows that the top plate 120 is in its uppermost position, that is, the massage bumps 98 are in their topmost position. FIG. 11 shows that the top plate 120 is in its lowermost position, that is, the massage bumps 98 are in their lowermost position.

Figure 12:
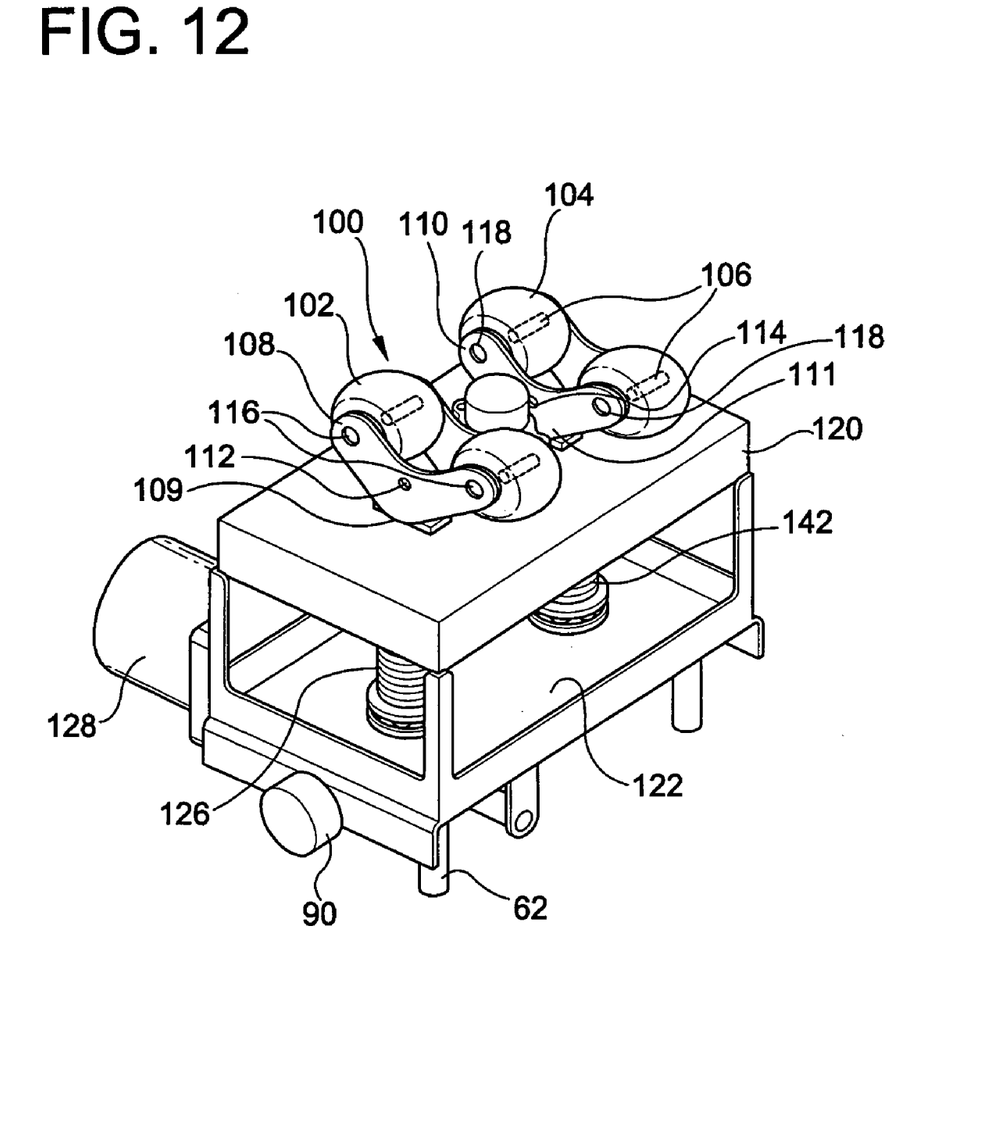
FIG. 12 is a perspective view showing different massage bumps.

FIG. 12 shows alternate massage bumps 100. The massage bumps 100 are preferably partitioned to first and second pairs 102, 104. Here, the first pair bumps 102 are aligned parallel to the second pair bumps 104. The massage bumps 100 each include a heater 106 which can be a heating lamp generating heat and infrared rays.

To further improve massaging effect, there are provided first and second bump holders 108, 110 propping and maintaining the first and second pair bumps 102, 104 above the top plate 120 of the lifter 20. For a better massaging result, the first and second bump holders 108, 110 are tapered toward each lower end 109, 111 thereof, and a first engagement member 112, 114 to rockingly engage the lower ends 109, 111 of the bump holders 108, 110 to the top plate 120 of the lifter 20, and a second engagement member 116, 118 to rollingly engage the massage bumps 100 thereto, are provided. The massage bumps 100 may be roller balls formed of precious stone such as jade.

Although the invention has been described in considerable detail, other versions are possible by converting the aforementioned construction. Therefore, the scope of the invention shall not be limited by the specification specified above.

What is claimed is:

1. A lie-down massager, comprising:
   a) a base frame having an elongated top panel, wherein an elongated top opening is formed centrally and lengthwise through the elongated top panel;
   b) a rider provided below the elongated top panel of the base frame;
   c) a guide member movably engaged between the base frame and the rider so as to enable the rider to make a horizontally reciprocal movement relative to the base frame;
   d) a lifter having a top plate and a bottom plate, a first nut, a first screw, and a motor, wherein the top plate has a top upper surface portion and a top lower surface portion, wherein the bottom plate has a bottom upper surface portion and a bottom lower surface portion, wherein the first screw is vertically and rotationally attached to the bottom upper surface portion, wherein the first nut is fixed to the top lower surface portion, wherein the first screw engages with the first nut so that rotation of the first screw lifts the first nut or lowers the first nut, wherein the motor rotates the first screw in either clockwise or counterclockwise direction, wherein the lifter further comprises a second screw vertically and rotationally attached to the bottom upper surface portion, and a second nut fixed to the top lower surface portion, wherein the second screw engages with the second nut so that rotation of the second screw lifts the second nut or lowers the second nut, wherein the first screw and the second screw are spaced from each other by a predetermined distance, wherein the first screw and the second screw are connected by a power transmission device so that they rotate together, wherein the power transmission device includes a first sprocket wheel that is fixed to the first screw, a second sprocket wheel that is fixed to the second screw, and a chain that is wound around the first sprocket wheel and the second sprocket wheel;
   e) massage bumps attached to the top upper surface portion of the lifter and moving vertically and/or horizontally along the elongated top opening of the elongated top panel of the base frame.

2. The lie-down massager of claim 1 further comprising a pad covering the massage bumps and the elongated top opening of the base frame.

3. The lie-down massager of claim 1 wherein the massage bumps are partitioned to first and second pairs, wherein the first pair bumps are aligned parallel to the second pair bumps.

4. The lie-down massager of claim 3 further comprising:
   a) first and second bump holders propping and maintaining the first and second pair bumps above the top plate of the lifter, wherein the first and second bump holders are tapered toward each lower end thereof; and
   b) a first engagement member to rockingly engage the lower ends of the bump holders to the top plate of the lifter.

5. The lie-down massager of claim 4 further comprising a second engagement member to rollingly engage the massage bumps thereto.

6. The lie-down massager of claim 4 wherein the massage bumps are roller balls.

7. The lie-down massager of claim 6 wherein the roller balls are formed of jade.

8. The lie-down massager of claim 1 wherein each of the massage bumps includes a heater.

9. The lie-down massager of claim 8 wherein the heater is a heating lamp generating heat and infrared rays.

10. The lie-down massager of claim 1 wherein the guide member comprises:
a) one or more roller gear engaged to and powered by a roller gear motor, wherein the roller gear motor is fixed to the rider; and
b) one or more side rack gears parallel to each other and provided lengthwise in the base frame;
wherein the roller gears are rollably connected to the rider and rotatably mounted on the side rack gears.

11. The lie-down massager of claim 1 wherein the guide member comprises:
a) rider guide rollers provided on each side of the rider, wherein the rider guide rollers are rollably engaged to the base frame to guide a horizontally reciprocal movement of the rider;
b) a pair of pulleys linked by a rope and respectively mounted in a front end portion and a rear end portion of the base frame, wherein a predetermined portion of the rope is fixedly attached to the rider so that the pulley rotation enables the rider to generate a horizontally reciprocal movement of the rider.

12. The lie-down massager of claim 11 wherein the pulleys are relatively twisted by 90 degrees against each other.

13. The lie-down massager of claim 1 further comprising:
a) a pair of roller coasters parallel to each other, wherein the roller coasters are attached to the base frame, wherein each of the roller coasters has a substantially waved top surface; and
b) coaster guide rollers formed outwardly extending from each side of the lifter, wherein the coaster guide rollers enable the lifter to make a roller coasting movement on and along the waved top surfaces of the roller coasters.

14. The lie-down massager of claim 13 wherein each of the waved top surfaces of the roller coasters substantially forms a curvature of a human spinal cord.

15. The lie-down massager of claim 13 wherein the lifter further comprises a plurality of elongated guides extending downward from the bottom lower surface portion of the bottom plate, and the rider further comprises a plurality of guide bushes upwardly formed on the rider to releasably receive the elongated guides so as to stabilize the roller coasting movement of the lifter along the roller coasters.

16. The lie-down massager of claim 15 wherein the elongated guides are shaped in pins.

17. The lie-down massager of claim 1 wherein the first nut and the second nut are integrated with the top plate of the lifter.

18. The lie-down massager of claim 1 wherein the lifter further comprises a worm wheel fixed to the first screw, and a worm gear fixed to the motor.

19. The lie-down massager of claim 18 wherein the massage bumps are partitioned to first and second pairs, wherein the first pair bumps are aligned parallel to the second pair bumps.

20. The lie-down massager of claim 19 further comprising:
a) first and second bump holders propping and maintaining the first and second pair bumps above the top plate of the lifter, wherein the first and second bump holders are tapered toward each lower end thereof;
b) a first engagement member to rockingly engage the lower ends of the bump holders to the top plate of the lifter; and
c) a second engagement member to rollingly engage the massage bumps thereto.

21. The lie-down massager of claim 20 further comprising:
a) a pair of roller coasters parallel to each other, wherein the roller coasters are attached to the base frame, wherein each of the roller coasters has a substantially waved top surface; and
b) coaster guide rollers formed outwardly extending from each side of the lifter, wherein the coaster guide rollers enable the lifter to make a roller coasting movement on and along the waved top surfaces of the roller coasters.

22. The lie-down massager of claim 21 wherein each of the waved top surfaces of the roller coasters substantially forms a curvature of a human spinal cord.

23. The lie-down massager of claim 22 wherein the lifter further comprises a plurality of elongated guides extending downward from the bottom lower surface portion, and the rider further comprises a plurality of guide bushes upwardly formed on the rider to releasably receive the elongated guides so as to stabilize the roller coasting movement of the lifter along the roller coasters.

24. The lie-down massager of claim 23 wherein each of the massage bumps includes a heating lamp generating heat and infrared rays.

25. The lie-down massager of claim 1 wherein the massage bumps are round projections fixed to the top upper surface portion of the lifter.

* * * * *